US011542480B2

(12) United States Patent
Kimura et al.

(10) Patent No.: US 11,542,480 B2
(45) Date of Patent: Jan. 3, 2023

(54) MUTANT GLYCINE OXIDASE DERIVED FROM THERMOPHILIC BACTERIUM BELONGING TO FAMILY BACILLUS, AND METHOD FOR PRODUCING SAME

(71) Applicant: NIPRO CORPORATION, Osaka (JP)

(72) Inventors: Takashi Kimura, Osaka (JP); Yasushi Tani, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 16/645,120

(22) PCT Filed: Sep. 10, 2018

(86) PCT No.: PCT/JP2018/033455
§ 371 (c)(1),
(2) Date: Mar. 6, 2020

(87) PCT Pub. No.: WO2019/050033
PCT Pub. Date: Mar. 14, 2019

(65) Prior Publication Data
US 2021/0238563 A1    Aug. 5, 2021

(30) Foreign Application Priority Data

Sep. 11, 2017    (JP) .............................. JP2017-174109

(51) Int. Cl.
*C12N 9/02* (2006.01)
*C12N 9/06* (2006.01)

(52) U.S. Cl.
CPC .... *C12N 9/0022* (2013.01); *C12Y 104/03019* (2013.01)

(58) Field of Classification Search
CPC .................................................. C12N 9/0022
See application file for complete search history.

(56) References Cited

U.S. PATENT DOCUMENTS

2016/0002610 A1    1/2016 Kodama et al.

FOREIGN PATENT DOCUMENTS

WO    2014157705 A1    10/2014

OTHER PUBLICATIONS

Heylen. K6D334_9BACI. UniProtKB Database. Jul. 5, 2017.*
Studer (Residue mutations and their impact on protein structure and function: detecting beneficial and pathogenic changes. Biochem. J. (2013) 449, 581-594.*
Equar, M. et al., "Purification and Properties of Glycine Oxidase from Pseudomonas putida KT2440," Journal of Natural Science and Vitaminology, vol. 61, 506-510, Dec. 2015, 5 pages.
Shiono T. et al., "Crystal structure of glycine oxidase from Geobacillus kaustophilus," Photon Factory Activity Report 2014 Part B (Biological Science No. 204), 2015, 1 page.
Martinez-Martinez, I. et al., "Characterization and structural modeling of a novel thermostable glycine oxidase from Geobacillus kaustophilus HTA426," Proteins Structure Function and Bioinformatics, vol. 70: 1429-1441, Mar. 2007, 13 pages.
Nishiya Y. et al., "Purification and characterization of a novel glycine oxidase from Bacillus subtilis," FEBS Letters, vol. 438, Issue 3, Nov. 6, 1998, 4 pages.
Rosini, E. et al., "Novel biosensors based on optimized glycine oxidase," The FEBS Journal, Jun. 9, 2014, 13 pages.

* cited by examiner

*Primary Examiner* — Yong D Pak
(74) *Attorney, Agent, or Firm* — Alleman Hall Creasman & Tuttle LLP

(57) ABSTRACT

A mutant glycine oxidase is obtained by substituting at least one wild-type amino acid sequence derived from thermophilic bacteria belonging to the family *Bacillus* with another amino acid, and has the following enzyme properties. Molecular weight: 40,000±2,000 daltons by SDS-PAGE. Optimum temperature: 45° C. under the condition of pH 8.5 in presence of pyrophosphate. Optimum pH: pH 8.0 under the condition of 37° C. in presence of pyrophosphate. Thermal stability: Stable up to 70° C. under the condition of pH 8.5 while retaining for 1 hour in presence of pyrophosphate. pH Stability: Stable in the range of pH 5.5 to 10.0 under the condition of 4° C. while retaining for 24 hours in presence of pyrophosphate. Specific activity: 1.2 units/mg or more. Kinetic constant $K_m$: 0.2 mM or less.

16 Claims, 3 Drawing Sheets

Specification includes a Sequence Listing.

Fig. 1

```
          10         20         30         40         50         60
    MTHRYDVAIV GGGVIGAAIG FELAKRRHRV AIFEKGTMGS GASSAAAGML GAQSEFSTSS 70         80         90        100        110        120
    PLVPLALQSR ALMPALAEEL RERTGIDIGL VEKGLIKLAT TEEEADDLYR HYTFWRGIGE 130        140        150        160        170        180
    PVQWLTKGEA LEMEPRLAAE ALAGAMYIPG DGQVSAPDLA AALAYAAASA GACLYEYTEV 190        200        210        220        230        240
    FDIRSDSSGH VLDTTGGTFA AEAVVIASGA WAARLGARVG LSLSVYPVKG ECVMVRAPVP 250        260        270        280        290        300
    LLQTTVFAKN GCYIVPKSGN RLLIGATSTP GTFDRRVSAG GVMNLLHRAA HLVPDIEQAE
                  ↓
                  X 310        320        330        340        350        360
    WVASWSGIRP QTEDGLPYLG EHPERRGLFV AAGHYRNGIL LSPLTGLLVA DLVERKETAF

370
    DLAPFSLTRH IGKVGVE
```

Fig. 2

```
ATGACGCATC GGTATGACGT CGCCATCGTC GGCGGCGGGG TGATTGGGGC    50
GGCCATCGGT TTTGAGCTCG CCAAGCGGCG GCATCGCGTC GCCATTTTTG   100
AAAAAGGAAC GATGGGAAGC GGGGCGTCAA GCGCGGCAGC CGGCATGCTT   150
GGGGCGCAAT CCGAGTTTTC GACGTCAAGC CCGCTTGTGC CGCTTGCCTT   200
GCAAAGCCGA GCTCTCATGC CGGCCTTGGC TGAAGAGCTG AGGGAGAGGA   250
CCGGCATCGA TATCGGCCTT GTCGAAAAAG GATTGATCAA ACTAGCGACA   300
ACGGAAGAGG AAGCAGACGA TCTCTATCGC CATTATACAT TTTGGCGGGG   350
CATAGGCGAA CCGGTGCAGT GGCTCACGAA AGGGGAGGCG CTTGAAATGG   400
AGCCGCGTCT TGCGGCGGAA GCGCTTGCCG GCGCGATGTA CATCCCTGGC   450
GATGGGCAAG TGAGCGCTCC GGATTTGGCC GCCGCTCTTG CCTATGCCGC   500
CGCCTCCGCC GGCGCTTGTC TGTACGAGTA TACGGAAGTG TTCGACATCC   550
GTTCCGACAG CAGTGGGCAT GTGTTAGACA CAACAGGCGG GACGTTTGCC   600
GCCGAGGCGG TCGTCATCGC TTCCGGCGCT TGGGCGGCGC GGCTCGGCGC   650
GCGGGTCGGG CTTTCGCTTT CCGTTATCCG GTCAAAGGA GAATGCGTCA   700
TGGTGCGCGC CCCGGTTCCG TTGTTGCAAA CGACTGTATT TGCGAAAAAC   750
GGCTGCTACA TCGTTCCGAA ATCAGGAAAC CGGCTGCTCA TCGGAGCGAC   800
↓↓↓
NNN
GTCCACGCCC GGCACGTTCG ATCGACGTGT ATCGGCCGGT GGGGTGATGA   850
ACTTGCTTCA CCGCGCCGCC CACCTTGTTC CGGACATCGA ACAGGCGGAA   900
TGGGTGGCAT CATGGAGCGG CATTCGGCCG CAGACCGAAG ACGGCTTGCC   950
TTATCTAGGC GAGCATCCGG AGCGGCGCGG CTTATTCGTC GCTGCCGGCC  1000
ATTACCGGAA CGGCATTTTG CTCAGCCCAT TGACCGGTCT GCTTGTCGCC  1050
GACTTAGTGG AGCGGAAAGA GACGGCGTTT GATCTTGCGC CATTTTCGTT  1100
GACACGCCAT ATCGGAAAGG TGGGGGTGGA ATGA                   1134
```

MUTANT GLYCINE OXIDASE DERIVED FROM THERMOPHILIC BACTERIUM BELONGING TO FAMILY BACILLUS, AND METHOD FOR PRODUCING SAME

TECHNICAL FIELD

The present invention relates to a mutant glycine oxidase derived from thermophilic bacteria belonging to the family *Bacillus* and a method for producing the same, and in particular, relates to a mutant glycine oxidase derived from thermophilic bacteria belonging to the family *Bacillus* and a method for producing the same, capable of achieving both good thermal stability and good enzyme activity.

BACKGROUND ART

Glycine is an amino acid having the simplest structure that has no stereoisomerism of D-form or L-form, and is one of the amino acids that constitute proteins, and it is also known as a raw material (starting material) for biosynthesis of various biological substances. As one of the methods for measuring glycine, a mechanical measurement method using mass spectrometry (MS), high performance liquid chromatography (HPLC), an amino acid analyzer or the like is known. However, in the mechanical measurement method, in general, a measuring instrument is expensive and maintenance cost is high, and operation requires skill.

Therefore, an enzyme measurement method using glycine oxidase that acts on glycine and the like have been proposed as a cheaper and simpler measurement method. One of typical glycine oxidases is known to be derived from *Bacillus subtilis*. For example, Non-PTL 1 has specifically reported on a glycine oxidase derived from *Bacillus subtilis*.

In addition, examples of glycine oxidase currently on the market include product number H244K manufactured by BioVision, Inc. This commercially available glycine oxidase is also derived from *Bacillus subtilis*, and is a mutant enzyme in which a mutation has been introduced into a wild-type glycine oxidase. Non-PTL 2 has specifically reported on the mutant glycine oxidase and also proposes a biosensor using the same.

Further, PTL 1 discloses a modified glycine oxidase in which at least one of amino acid residues is displaced to modify properties such as enzyme activity, thermal stability, and substrate specificity, and a method for analyzing glycine using the same. The modified glycine oxidase specifically disclosed in the Examples of PTL 1 is also derived from *Bacillus subtilis*, and is obtained by introducing a mutation of an amino acid residue into a wild-type glycine oxidase.

CITATION LIST

Patent Literature

PTL 1: WO 2014/157705 A

Non-Patent Literature

Non-PTL 1: Yoshiaki Nishiya, Tadayuki Imanaka, "Purification and characterization of a novel glycine oxidase from *Bacillus subtilis*" FEBS (Federation of European Biochemical Societies) Letter Vol. 438 pp. 263-266 (1998)

Non-PTL 2: Elena Rosini, Luciano Piubelli, Gianluca Molla, Luca Frattini, Mattia Valentino, Antonio Varriale, Sabato D'Auria and Loredano Pollegioni, "Novel biosensors based on oprimized glycine oxidase" FEBS (Federation of European Biochemical Societies) Journal Vol. 281 pp. 3460-3472 (2014)

SUMMARY OF INVENTION

Technical Problem

The modified glycine oxidase disclosed in PTL 1 certainly allows modification of properties such as enzyme activity, thermal stability, and substrate specificity, with respect to the wild-type. For example, its specific activity and the like are about the same as those of commercially available glycine oxidase.

In addition, in recent years, in order to improve industrial applicability, various enzymes are required to have thermal stability (or heat resistance) that can maintain good enzyme activity even under higher temperature conditions. PTL 1 also attempts to improve thermal stability by modifying a wild-type glycine oxidase, but recently, there is a tendency to require even better thermal stability.

The present invention has been made to solve such problems, and an object of the present invention is to provide a mutant glycine oxidase derived from bacteria and a method for producing the same, capable of achieving good thermal stability as well as good enzyme activity.

Solution to Problem

In order to solve the above-described problem, the mutant glycine oxidase according to the present invention is a mutant glycine oxidase which is a mutant enzyme in which at least one amino acid sequence in a wild-type glycine oxidase derived from thermophilic bacteria belonging to the family *Bacillus* is substituted with another amino acid, and has the following configurations: the molecular weight is 40,000±2,000 daltons in SDS-polyacrylamide gel electrophoresis, the optimum temperature is 45° C. under a condition of pH 8.5 in presence of pyrophosphate; the optimum pH is pH 8.0 under a condition of 37° C. in presence of pyrophosphate; thermal stability is stable up to 70° C. under a condition of pH 8.5 while retaining for 1 hour in presence of pyrophosphate; pH stability is stable in the range of pH 5.5 to 10.0 under a condition of 4° C. while retaining for 24 hours in presence of pyrophosphate; the specific activity is 1.2 units/mg or more; and the kinetic constant (Michaelis constant) $K_m$ is 0.2 mM or less.

According to the above configurations, the mutant glycine oxidase achieves the above enzyme properties by introducing a mutation into the wild-type glycine oxidase derived from thermophilic bacteria belonging to the family *Bacillus*. This mutant glycine oxidase can maintain a kinetic constant $K_m$ that is substantially in the same range as that of the conventional mutant glycine oxidase, and also can achieve high thermal stability as compared not only with the conventional mutant glycine oxidase but also with the wild-type glycine oxidase, and further achieves high specific activity as compared with the conventional mutant glycine oxidase and the wild-type glycine oxidase. Thereby, in the mutant glycine oxidase, it is possible to achieve good thermal stability as well as good enzyme activity.

In the mutant glycine oxidase of the above configuration, a glycine in a partial amino acid sequence that binds in the order of asparagine (N), glycine (G), cysteine (C), and tyrosine (Y) contained in the amino acid sequence of the wild-type glycine oxidase is substituted with another amino acid may be configured.

Also, in order to solve the above-described problem, the mutant glycine oxidase according to the present invention may be configured as a mutant enzyme of glycine oxidase derived from thermophilic bacteria belonging to the family *Bacillus* showing 95% or more homology to an amino acid sequence represented by SEQ ID NO: 1, having an amino acid sequence in which a 251st amino acid in the amino acid sequence represented by SEQ ID NO: 1 is substituted from glycine to another amino acid.

According to the above configuration, the mutant glycine oxidase is one obtained by introducing a mutation into the wild-type glycine oxidase derived from thermophilic bacteria belonging to the family *Bacillus* at the above position. This mutant glycine oxidase can maintain a kinetic constant $K_m$ that is substantially in the same range as that of the conventional mutant glycine oxidase, and also can achieve high thermal stability as compared not only with the conventional mutant glycine oxidase but also with the wild-type glycine oxidase, and further achieves high specific activity as compared with the conventional mutant glycine oxidase and the wild-type glycine oxidase. Thereby, in the mutant glycine oxidase, it is possible to achieve good thermal stability as well as good enzyme activity.

In addition, in the mutant glycine oxidase of the above configuration, it may be a configuration having an amino acid sequence in which the 251st amino acid in the amino acid sequence represented by SEQ ID NO: 1 is substituted from glycine to a basic amino acid or a hydrophobic amino acid.

Moreover, in the mutant glycine oxidase of the above configuration, it may be configured that the basic amino acid is glutamine, arginine, or histidine, and the hydrophobic amino acid is isoleucine or threonine.

Further, in the mutant glycine oxidase of the above configuration, it may be configured that the another amino acid is alanine, glutamic acid, histidine, isoleucine, asparagine, glutamine, arginine, or threonine.

Furthermore, in the mutant glycine oxidase of the above configuration, it may be configured that the thermophilic bacteria belonging to the family *Bacillus* is a bacteria belonging to the genus *Bacillus*, the genus *Alicyclobacillus*, the genus *Brevibacillus*, the genus *Geobacillus*, the genus *Sulfobacillus*, the genus *Paenibacillus*, or the genus *Salinicoccus*.

Also, the present invention includes a DNA encoding the mutant glycine oxidase of the above configuration.

In addition, the present invention also includes a replicable recombinant DNA containing the DNA of the above configuration and an autonomously replicable vector.

Moreover, the present invention also includes a cell obtained by introducing the DNA of the above configuration or the recombinant DNA of the above configuration into a host cell.

Further, the present invention also includes a method for producing a mutant glycine oxidase including culturing the cells of the above configuration, and collecting the mutant glycine oxidase from the resulting culture.

The above object, other objects, features, and advantages of the present invention will become apparent from the following detailed description of preferred embodiments with reference to the accompanying drawings.

SEQUENCE LISTING

The nucleotide and amino acid sequences for the wild-type and mutant glycine oxidase described herein are listed in the sequence listing entitled "Mutated Glycine Oxidase derived from *Bacillus* family," created on Dec. 17, 2020, and having a file size of 11 KB, the entirety of which is hereby incorporated by reference for all purposes.

Advantageous Effects of Invention

In the present invention, an effect that a mutant glycine oxidase derived from bacteria and a method for producing the same, capable of achieving good thermal stability as well as good enzyme activity, can be provided is exhibited by the above configuration.

BRIEF DESCRIPTION OF DRAWINGS

FIG. 1 is a sequence diagram showing SEQ ID NO: 1, which is an amino acid sequence of a wild-type glycine oxidase exemplified in an embodiment of the present invention, with a mutation corresponding to SEQ ID NO: 3 indicated in the dashed box.

FIG. 2 is a sequence diagram showing SEQ ID NO: 2, which is a nucleotide base sequence of DNA encoding the wild-type glycine oxidase having the amino acid sequence of FIG. 1, with a mutation corresponding to SEQ ID NO: 4 indicated in the dashed box.

DESCRIPTION OF EMBODIMENTS

Figure 3A:
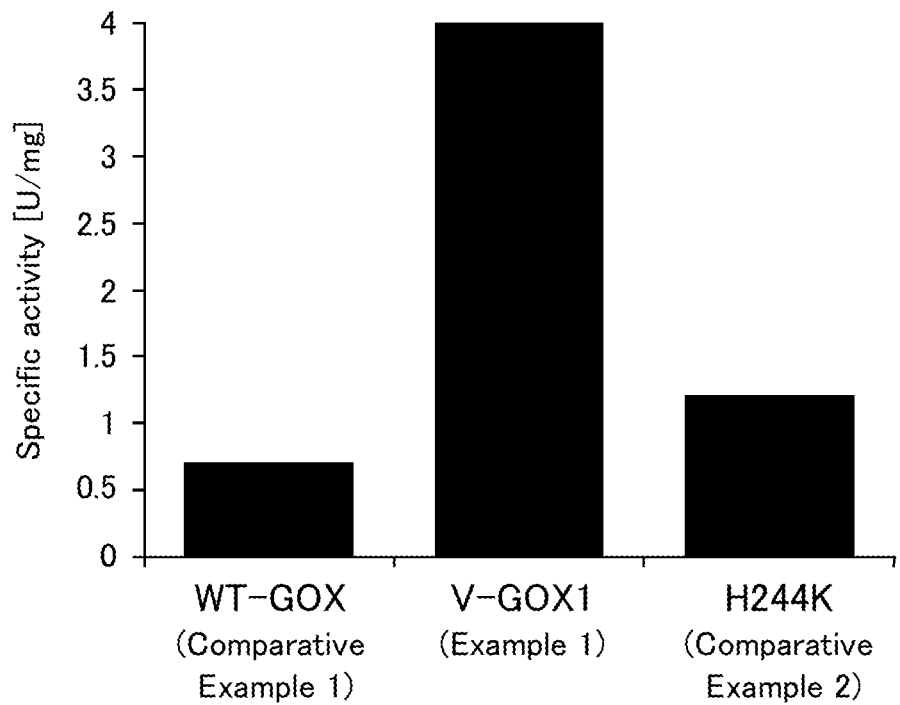
FIG. 3A is a graph comparing specific activities of each of glycine oxidases in example and comparative examples.

The mutant glycine oxidase derived from bacteria according to the present disclosure is a mutant enzyme in which at least one of the amino acid sequences in the wild-type glycine oxidase derived from thermophilic bacteria belonging to the family *Bacillus* is substituted with another amino acid, and it has characteristic enzyme properties even compared with the conventional glycine oxidase.

[Thermophilic Bacteria Belonging to Family *Bacillus*]

The thermophilic bacteria belonging to the family *Bacillus* from which the mutant glycine oxidase according to the present disclosure is derived is not particularly limited as long as they are bacteria that are classified as Bacillaceae and have thermophilicity. The term "thermophilicity" as used herein means that the optimum growth temperature of the bacteria is 45° C. or more or the growth limit temperature of the bacteria is 55° C. or more, or both are satisfied.

Specific examples of the bacteria belonging to the family *Bacillus* include bacteria belonging to the genus *Bacillus*, the genus *Alicyclobacillus*, the genus *Anoxybacillus*, the genus *Brevibacillus*, the genus *Geobacillus*, the genus *Halobacillus*, the genus *Oceanobacillus*, the genus *Paenibacillus*, the genus *Sulfobacillus*, the genus *Virgibacillus*, or the genus *Salinicoccus*, but are not particularly limited.

In the examples described later, *Geobacillus kaustophilus* HTA426 strain is used as the thermophilic bacteria belonging to the family *Bacillus*. A wild-type glycine oxidase derived from this *Geobacillus kaustophilus* HTA426 strain has a characteristic region having high homology with the amino acid sequences of glycine oxidases derived from each of *Geobacillus stearothermophilus*, *Geobacillus thermoleovorans*, *Geobacillus thermodenitrificans* and *Geobacillus subterraneus*, which are other thermophilic bacteria belonging to the family *Bacillus*.

As a commercially available glycine oxidase, a mutant enzyme derived from *Bacillus subtilis*, which is a non-thermophilic *Bacillus* bacterium, is known as described above. For convenience of explanation, among the glycine oxidases derived from *Bacillus subtilis*, the wild type is referred to as "*B. subtilis* wild-type glycine oxidase", and the mutant type is referred to as "*B. subtilis* mutant glycine oxidase". Moreover, the glycine oxidase derived from the *Geobacillus kaustophilus* (*G. kaustophilus*) strain HTA426 strain is also referred to as "*G. kaustophilus* wild-type glycine oxidase" for convenience of explanation.

The three-dimensional structure of *B. subtilis* wild-type glycine oxidase has been reported, for example, in Non-PTL 2, and the three-dimensional structure of *G. kaustophilus* wild-type glycine oxidase has been reported, for example, in Reference Literature 1: Takako Shiono, Takaomi Nomura, Yoshiaki Nishiya, Ryoichi Arai, "Crystal structure of glycine oxidase from *Geobacillus kaustophilus*" Photon Factory Activity Report 2014 #32, PART B, Users' Report (Biological Science, No. 204), 2015.

In *B. subtilis* wild-type glycine oxidase, seven types of motifs are known, and for example, in the examples of Non-PTL 2 and PTL 1, mutations are introduced into one of these motifs, an HCY motif. The HCY motif is located in a pathway where a substrate such as glycine goes to the active center of glycine oxidase.

While *G. kaustophilus* wild-type glycine oxidase has thermal stability superior to that of *B. subtilis* mutant glycine oxidase, as demonstrated experimentally in the examples described later, the enzyme activity is greatly inferior.

Therefore, the present inventors have considered that enzyme activity can be improved while maintaining thermal stability when a mutation is also introduced into the wild-type HCY motif or at a position corresponding to the HCY motif, also in the *G. kaustophilus* wild-type glycine oxidase, similarly to the *B. subtilis* mutant glycine oxidase, and intensively studied. However, when comparing the amino acid sequences between the *G. kaustophilus* wild-type glycine oxidase and the *B. subtilis* wild-type glycine oxidase, it has been revealed that the *G. kaustophilus* wild-type glycine oxidase has a characteristic region that is not be seen in the *B. subtilis* wild-type glycine oxidase.

As shown in FIG. 1, this characteristic region is a partial amino acid sequence that binds in the order of a 250th asparagine (N), a 251st glycine (G), a 252nd cysteine (C), and a 253rd tyrosine (Y) in the amino acid sequence of the *G. kaustophilus* wild-type glycine oxidase. In addition, it has been also revealed that this characteristic region has high homology with the amino acid sequences of glycine oxidases derived from other thermophilic bacteria belonging to the family *Bacillus*, as described above.

Therefore, as will be explained in the examples described later, when an attempt was made to introduce a mutation into this characteristic region, it has been revealed that, in addition to the fact that, in the mutant glycine oxidase in which the 251st glycine was substituted with another amino acid, the enzyme activity is improved more than in the wild-type, the thermal stability is improved rather than being maintained, and that the kinetic constant (Michaelis constant) $K_m$ is also lower than that of the wild-type.

Accordingly, it can be said that the mutant glycine oxidase according to the present disclosure introduces a mutation into a characteristic region that is widely conserved in the thermophilic bacteria belonging to the family *Bacillus*, with respect to the wild-type glycine oxidase derived from the thermophilic bacteria belonging to the family *Bacillus*, whereby not only the enzyme activity is improved, but also unexpected and excellent enzyme properties are obtained.

Therefore, the thermophilic bacteria belonging to the family *Bacillus* from which the mutant glycine oxidase according to the present disclosure is derived may be any bacteria as long as they are classified as Bacillaceae and have thermophilicity, as described above. Typical examples thereof include thermophilic bacteria belonging to the genus *Geobacillus*, and a more preferred example includes *Geobacillus kaustophilus*.

Further, as described above, the thermophilic bacteria belonging to the genus *Geobacillus* include, in addition to *G. kaustophilus*, *G. stearothermophilus*, *G. thermoleovorans*, *G. thermodenitrificans* and *G. subterraneus*, *Geobacillus thermoglucosidasius*, *Geobacillus calboxylosilyticus*, *Geobacillus tepidamans*, *Geobacillus galactosidasius*, *Geobacillus zalihae*, other unclassified strains of the genus *Geobacillus* (*Geobacillus* sp.), and the like, but are not particularly limited.

Here, for example, in Reference Literature 2: Messele Yohannes EQUAR, Yasushi TANI, Hisaaki MIHARA "Purification and Properties of Glycine Oxidase from *Pseudomonas putida* KT2440" Journal of Nutritional Science and Vitaminology, Vol. 61 pp. 506-510 (2015), a phylogenetic analysis of glycine oxidase homology has been shown, and based on this analysis, it has been revealed that the genera *Bacillus*, *Alicyclobacillus*, *Brevibacillus*, *Geobacillus*, *Sulfobacillus*, *Paenibacillus*, and *Salinicoccus* had differentiated from the same strain. In other words, it can be seen that there is a high possibility that the characteristic region is preserved, at least in glycine oxidases derived from each of the genus described above, among the *Bacillus* bacteria.

Therefore, in the present disclosure, a more preferable example of the thermophilic bacteria belonging to the family *Bacillus* from which glycine oxidase is derived can include, other than the genus *Geobacillus*, thermophilic bacteria belonging to the genus *Bacillus*, the genus *Alicyclobacillus*, the genus *Brevibacillus*, the genus *Sulfobacillus*, the genus *Paenibacillus*, or the genus *Salinicoccus*.

[Mutant Glycine Oxidase]

The mutant glycine oxidase according to the present disclosure is obtained by introducing a mutation into a wild-type glycine oxidase derived from thermophilic bacteria belonging to the family *Bacillus*, as described above, and it may be any one having the characteristic enzyme properties shown in (1) to (7) below, as also shown in the examples described later.

(1) The molecular weight is 40,000±2,000 daltons in SDS-polyacrylamide gel electrophoresis (SDS-PAGE).

(2) The optimum temperature is 45° C. under the condition of pH 8.5 in presence of pyrophosphate.

(3) The optimum pH is pH 8.0 under the condition of 37° C. in presence of pyrophosphate.

(4) Thermal stability is stable up to 70° C. under the condition of pH 8.5 while retaining for 1 hour in presence of pyrophosphate.

(5) pH Stability is stable in the range of pH 5.5 to 10.0 under the condition of 4° C. while retaining for 24 hours in presence of pyrophosphate.

(6) The specific activity is 1.2 units/mg or more.

(7) The kinetic constant (Michaelis constant) $K_m$ is 0.2 mM or less.

Here, among the above enzyme properties, (1) the molecular weight is based on the molecular weight of wild-type glycine oxidase, but may be within the range of 39,000±1,000 daltons. In addition, (6) the specific activity is preferably 2.4 units/mg or more, and more preferably 4.0 units/mg or more.

In the present disclosure, the enzyme properties (1) to (7) can be evaluated based on "Evaluation of Various Properties of Glycine Oxidase" in the examples described later, and may be evaluated by other known methods.

More specific mutant glycine oxidase can include the mutant glycine oxidase derived from the *Geobacillus kaustophilus* HTA426 strain described in detail in the examples, as described above. This mutant glycine oxidase can include those having an amino acid sequence in which a 251st amino acid in the amino acid sequence represented by SEQ ID NO: 1 is substituted from glycine to another amino acid, as shown in FIG. 1, that is, those having an amino acid sequence shown in SEQ ID NO: 3 for sequence. In SEQ ID NO: 3, the 251st (position 251) amino acid is indicated by an arbitrary amino acid Xaa, and FIG. 1 shows that it is substituted with an arbitrary amino acid X by an arrow.

Of course, the mutant glycine oxidase according to the present disclosure is not limited to one in which the 251st (position 251) glycine in the amino acid sequence shown in SEQ ID NO: 1 is mutated (having the amino acid sequence of SEQ ID NO: 3), and it may be any one having the characteristic enzyme properties of (1) to (7) above. However, when SEQ ID NO: 1 is used as a reference, it may be any one having 95% or more homology (or a sequence identity), more preferably any one having 97% or more homology, and further preferably any one having 98% or more homology to the amino acid sequence shown in SEQ ID NO: 1.

In addition, the mutant glycine oxidase according to the present disclosure, as explained in the examples described later, when SEQ ID NO: 1 is used as a reference, it is preferable that the 251st (position 251) glycine is one having an amino acid sequence substituted with another basic amino acid or a hydrophobic amino acid. Thereby, it is possible to achieve better enzyme activity as compared with the wild-type glycine oxidase. Specific basic amino acids are not particularly limited, and can include glutamine, arginine, histidine, or the like. Also, specific hydrophobic amino acids are not particularly limited, and can include isoleucine or threonine. Alternatively, as explained in the examples described later, another amino acid may be any one of alanine, glutamic acid, histidine, isoleucine, asparagine, glutamine, arginine, or threonine.

As described above, the mutant glycine oxidase according to the present disclosure is one that achieves the above enzyme properties by introducing a mutation into the wild-type glycine oxidase derived from thermophilic bacteria belonging to the family *Bacillus*. This mutant glycine oxidase can maintain a kinetic constant $K_m$ that is substantially in the same range as that of the conventional mutant glycine oxidase, also, high thermal stability can be achieved as compared not only with the conventional mutant glycine oxidase but also with the wild-type glycine oxidase, and furthermore, high specific activity can be achieved as compared with the conventional mutant glycine oxidase and the wild-type glycine oxidase. Therefore, according to the present disclosure, it is possible to obtain a mutant glycine oxidase capable of achieving good thermal stability as well as good enzyme activity.

[DNA Encoding Mutant Glycine Oxidase]

The present disclosure also includes DNA encoding the mutant glycine oxidase of the above configuration. SEQ ID NO: 2 in the sequence listing shows a base sequence encoding glycine oxidase derived from the *Geobacillus kaustophilus* HTA426 strain, and a typical example of the DNA according to the present disclosure include a DNA having a base sequence into which a mutation has been introduced in the base sequence shown in SEQ ID NO: 2.

As such a DNA, for example, as shown in FIG. 2, a codon composed of nucleotides 751 to 753 in the base sequence represented by SEQ ID NO: 2 in the sequence listing is a DNA having a base sequence substituted from a codon of guanine-guanine-cytosine (GGC) encoding glycine to a codon encoding another amino acid, that is, a DNA having a base sequence shown in SEQ ID NO: 4 in the sequence listing. In SEQ ID NO: 4, the nucleotides 751 to 753 encoding the 251st amino acid are indicated by n as an arbitrary nucleotide, and FIG. 2 shows they are substituted with an arbitrary nucleotide N by an arrow.

As described above, a DNA having the base sequence shown in SEQ ID NO: 2 is a DNA encoding the wild-type glycine oxidase derived from the *Geobacillus kaustophilus* HTA426 strain. Accordingly, the DNA having the base sequence shown in SEQ ID NO: 4 can be said to be a DNA in which the codon corresponding to the 251st glycine is substituted with a codon encoding another amino acid in the DNA encoding the wild-type glycine oxidase.

Here, the DNA according to the present disclosure is not limited to the DNA having the base sequence shown in SEQ ID NO: 4, and for example, may be a DNA having a base sequence homologous to the base sequence shown in SEQ ID NO: 4, or a DNA having another base sequence encoding the amino acid sequence shown in SEQ ID NO: 3. Further, the DNA according to the present disclosure may be a mutant DNA in which a mutation is introduced at a position excluding a codon corresponding to the 251st amino acid in the base sequence shown in SEQ ID NO: 4. This mutant DNA includes those having a base sequence in which one or two or more bases are deleted, substituted or added in the base sequence shown in SEQ ID NO: 4 within the range that retains an activity of a mutant glycine oxidase to be encoded. The number of bases to be deleted, substituted or added is usually within the range of 1 to 120, preferably within the range of 1 to 60, and more preferably within the range of 1 to 30.

The present disclosure also includes a replicable recombinant DNA containing a DNA encoding the mutant glycine oxidase of the above configuration and an autonomously replicable vector. A typical example of such an autonomously replicable vector includes a plasmid vector.

Specific plasmid vectors include pBR plasmids such as pBR322; pUC plasmids such as pUC18, pUC19, pUC118, and pUC119; pBS plasmids such as pBlueScript II, pBluescript II SK(+/−), pBluescript II KS(+/−), pBluescript II XR, and pBluescript II RI; pET plasmids such as pET-3a to 3d, pET-11a to d, pET-14b, pET-15b, and pET-21a to 21d; pGEX plasmids such as pGEX-1, pGEX-2T, and pGEX-3X; pTZ plasmids such as pTZ4, pTZ5, pTZ12, pTZ-18R, and pTZ-19R; pSU plasmids such as pSUO, pSU7, pSU22, and pSU23; genus *Bacillus* plasmids such as pUB110, pC194, pHY plasmids, pNU plasmids, pNY326, and pNC plasmids; shuttle vector plasmids such as pHV14, TRp7, YEp plasmids, and pBS7; and the like.

These plasmids can be appropriately selected according to various conditions such as the type of cell serving as a host and the type of expression system. In addition, the autonomously replicable vector may be a phage vector or the like.

The method for inserting the DNA encoding the mutant glycine oxidase of the above configuration into an autonomously replicable vector is not particularly limited, and a known method can be suitably used. General examples include a method of digesting (cutting) a DNA (or gene) encoding a mutant glycine oxidase and a vector with a known type II restriction enzyme, and annealing these DNA fragments and vector fragments as necessary, then ligating using DNA ligase and the like, but are not particularly limited.

The replicable recombinant DNA of the above configuration may contain the DNA encoding the mutant glycine oxidase of the above configuration and a DNA other than the autonomously replicable vector. For example, a DNA encoding a control sequence not contained in the autonomously replicable vector may be contained, or a DNA (or gene or the like) encoding another protein or peptide may be contained. At this time, the mutant glycine oxidase of the above configuration may be incorporated into a replicable recombinant DNA so as to constitute a chimeric protein together with other proteins and peptides.

[Method for Producing Mutant Glycine Oxidase, Etc.]

Such recombinant DNA can be introduced into cells that serve as known hosts. Accordingly, the present disclosure also includes a transformant obtained by introducing a replicable recombinant DNA containing a DNA encoding the mutant glycine oxidase of the above configuration and an autonomously replicable vector into a host cell. Examples of the host cells generally include microorganisms such as *Escherichia coli*, *Bacillus subtilis*, actinomycetes, and yeast, but are not limited thereto, and may be plant cells or animal cells.

In the examples described later, *Escherichia coli* is used for both the host cell for replicating the replicable recombinant DNA and the host cell for producing the mutant glycine oxidase of the above configuration from the replicated recombinant DNA. However, the present disclosure is not limited thereto, and for example, when replicating a replicable recombinant DNA, *Escherichia coli* may be used as the host cell, and when producing the mutant glycine oxidase of the above configuration, *Bacillus subtilis*, that is, bacteria belonging to the genus *Bacillus* may be used as the host cell. Also, in recent years, a protein expression system using bacteria belonging to the genus *Brevibacillus*, which is one of *Bacillus* bacteria, has been constructed and marketed. Therefore, when producing the mutant glycine oxidase of the above configuration, bacteria belonging to the genus *Brevibacillus* may be used as the host cell.

The method for introducing the recombinant DNA of the above configuration into the host cell, that is, the transformation method, is not particularly limited, and a known method according to the type of the host cell or the type of the autonomously replicable vector can be used. In the case of bacteria such as *Escherichia coli*, examples of typical transformation methods can include an electroporation method, a method of making cells into competent cells using calcium chloride, and the like. In the case where the host cell is yeast, a method of partially removing cell walls of the yeast cells to make spheroplast, a lithium acetate method, or the like can be used. In addition, in the case where the host cell is a fungus, a plant cell, or an animal cell, a particle gun method, a transfection method or the like can also be used.

Furthermore, the present disclosure includes not only a transformant obtained by introducing a recombinant DNA containing the DNA encoding the mutant glycine oxidase of the above configuration and an autonomously replicable vector into the host cell, but also cells in which the DNA encoding the mutant glycine oxidase of the above configuration has been introduced into a genome of the host cell. The method for introducing the DNA encoding the mutant glycine oxidase of the above configuration into the genome of the host cell is not particularly limited, and for example, when the host cell is *Saccharomyces cerevisiae* or its related species, the DNA can be integrated into a chromosome, using a YIp plasmid. Also, regardless of the type of the host cell, the DNA can be integrated into a chromosome or the like using a genome editing technique.

The transformant or DNA-integrated cell thus obtained may be cultured using a known nutrient medium according to various conditions such as the type of the host cell or the purpose of culture. For example, when replicating recombinant DNA using *Escherichia coli* as a host, an LB medium (LB broth) or the like may be used. Moreover, in the case of producing the mutant glycine oxidase of the above configuration by culturing the transformant of the above configuration or the DNA-integrated cell of the above configuration, a known culture medium (broth) corresponding to the type of the transformant or cell may be used. Further, various known additional components may be added to a culture medium according to various conditions.

As described above, the mutant glycine oxidase according to the present disclosure can be produced by introducing (or integrating) the DNA encoding the mutant glycine oxidase into a host cell by various methods to prepare a transformant (or DNA-integrated cell), and culturing the obtained transformant (or DNA-integrated cell). Therefore, the present disclosure also includes a method for producing a mutant glycine oxidase, including culturing such cells and collecting the mutant glycine oxidase of the above configuration from the obtained culture.

In the method for producing a mutant glycine oxidase according to the present disclosure, a cell culture scale is not particularly limited. For example, when a liquid medium (broth) is used, it may be a small-scale culture using a test tube or a flask, may be a large-scale culture using a jar fermenter, or may be a large-scale culture using a tank at an industrial level.

A method for collecting the mutant glycine oxidase of the above configuration from the cultured cells is not particularly limited, and a known method can be used. When the expressed mutant glycine oxidase accumulates in the cells, the mutant glycine oxidase may be collected by collecting the cultured cells, disrupting the cells by a known method to obtain a crude enzyme solution, and purifying or concentrating the crude enzyme solution by a known method. When it is not necessary to purify or concentrate, the above crude enzyme solution may be used as the mutant glycine oxidase according to the present disclosure. In addition, when the expressed mutant glycine oxidase is significantly secreted extracellularly, the mutant glycine oxidase may be collected from the entire culture including the cultured cells and the broth.

Thus, the mutant glycine oxidase according to the present disclosure can maintain a kinetic constant $K_m$ that is substantially in the same range as that of the conventional mutant glycine oxidase, also, high thermal stability can be achieved as compared not only with the conventional mutant glycine oxidase but also with the wild-type glycine oxidase, and further achieves high specific activity as compared with the conventional mutant glycine oxidase and the wild-type glycine oxidase. Therefore, the mutant glycine oxidase according to the present disclosure can be suitably used for enzyme measurement of glycine.

Further, the mutant glycine oxidase according to the present disclosure can be easily produced by introducing a DNA encoding the mutant glycine oxidase into a host cell, or the like, as described above. Therefore, it is also possible to mass-produce the mutant glycine oxidase according to the present disclosure at an industrial level, and also possible to stably provide, for example, as a reagent for enzyme measurement of glycine, a reagent for automatic measurement system of glycine, or the like.

EXAMPLES

The present invention will be described more specifically based on examples and comparative examples, but the present invention is not limited thereto. Those skilled in the art can make various changes, modifications, and alterations without departing from the scope of the present invention. Here, *Bacillus* bacteria used in the following examples and comparative examples, a cloning method, enzyme activity measurement and the like were performed as shown below.

(*Bacillus* Bacteria)

As *Bacillus* bacteria derived from a wild-type glycine oxidase in this example, *Geobacillus kaustophilus* HTA426 strain was used (for convenience of explanation, the *Geobacillus kaustophilus* HTA426 strain is hereinafter abbreviated as "HTA426"). HTA426 is available, for example, from the National Research and Development Agency, RIKEN BioResource Research Center (RIKEN BRC) Microbe Division (JCM) (JCM12893).

(Cloning of Glycine Oxidase)

Cloning of glycine oxidase from HTA426 was performed according to the method described in Non-PTL 1. However, a plasmid vector of pET-15b was used as a vector, and *E. coli* BL21 (DE3) was used as a host cell (host).

(Measurement of Enzyme Activity of Glycine Oxidase)

The enzyme activity of glycine oxidase was also measured according to the method described in Non-PTL 1.

Here, an assay buffer composed of 1 mM sodium pyrophosphate (pH 8.5), 5 mM 4-aminoantipyrine, and 20 mM phenol was used, and the optimal conditions were set to 37° C. in presence of 10 mM pyrophosphate and 1 mM glycine (substrate).

The method for measuring the enzyme activity of glycine oxidase in this example, that is, the method for measuring enzyme activity performed according to the method described in Non-PTL 1 using the above assay buffer is referred to as "this glycine oxidase activity measurement method".

(Evaluation of Various Properties of Glycine Oxidase)

Various properties of glycine oxidase were evaluated according to the conditions and/or methods described below.

(1) The molecular weight was determined by SDS-polyacrylamide gel electrophoresis (SDS-PAGE) according to the method described in Non-PTL 1.

(2) The optimum temperature was evaluated by varying measurement temperature within the range of 25° C. to 45° C. in this glycine oxidase activity measurement method.

(3) The optimum pH was evaluated by varying pH using a 10 mM phosphate buffer (pH 7.0 to 7.5), a 10 mM HEPES buffer (pH 7.5 to 8.0), a 10 mM pyrophosphate buffer (pH 8.0 to 8.5), and a pyrophosphate and carbonate mixed buffer (5 mM pyrophosphate and 5 mM carbonate buffer, pH 9.0 to 10.0), respectively, in place of the assay buffer, in this glycine oxidase activity measurement method.

(4) Thermal stability was determined by varying reaction temperature within the range of 30° C. to 90° C., and incubating for 15 minutes or 1 hour, then measuring the remaining enzyme activity, in this glycine oxidase activity measurement method, and evaluated as a relative activity based on the enzyme activity at 37° C.

(5) pH Stability was determined by using a 100 mM phosphate buffer (pH 5.5 to 7.5), a 10 mM pyrophosphate buffer (pH 8.0 to 8.5), and a pyrophosphate and carbonate mixed buffer (5 mM pyrophosphate and 5 mM carbonate buffer, pH 9.0 to 10.0), in place of the assay buffer, and incubating under the condition of 4° C. for 24 hours, then measuring the remaining enzyme, in this glycine oxidase activity measurement method, and evaluated as a relative activity based on the enzyme activity at pH 8.5.

(6) The specific activity was calculated by dividing the enzyme activity (unit: unit [U]) of the enzyme sample used in this glycine oxidase activity measurement method by the enzyme mass (unit: mg) contained in the enzyme sample. The enzyme mass is the mass of a protein contained in the enzyme sample, and was quantified by measuring the absorbance at 595 nm by Bradford method.

(7) The kinetic constant (Michaelis constant) $K_m$ was calculated based on Michaelis-Menten equation, by varying substrate concentration and measuring the enzyme activity, in this glycine oxidase activity measurement method.

Comparative Example 1

Figure 3B:
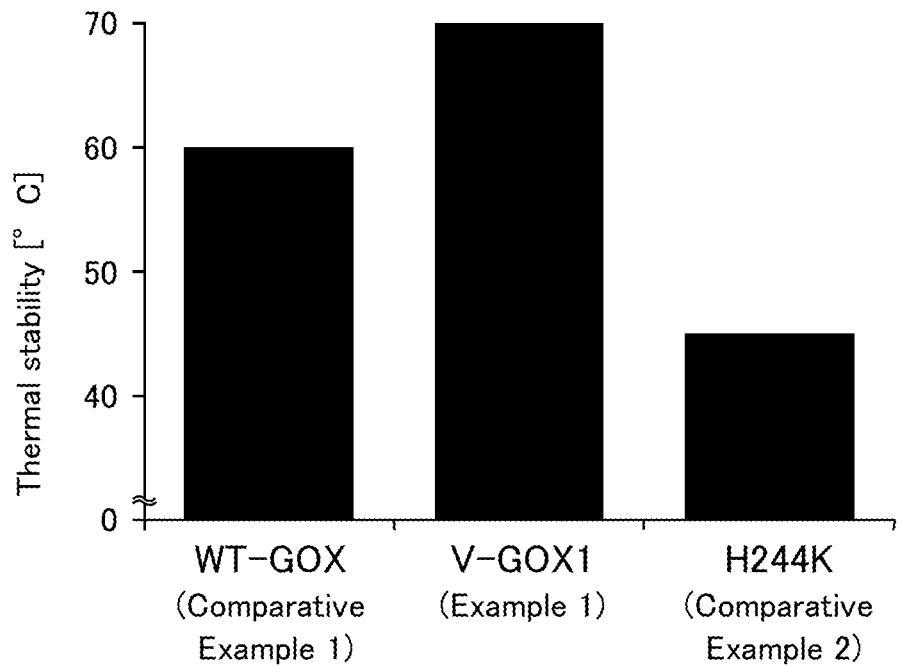
FIG. 3B is a graph comparing thermal stability of each of glycine oxidases in example and comparative examples.

The specific activity, thermal stability, and kinetic constant $K_m$ of the wild-type glycine oxidase derived from HTA426 were evaluated as described above. The results are shown in Table 1, the specific activity is shown in FIG. 3A, and thermal stability is shown in FIG. 3B.

The amino acid sequence of the wild-type glycine oxidase is shown in SEQ ID NO: 1 in FIG. 1 and the sequence listing, and the base sequence of the gene (DNA) encoding the wild-type glycine oxidase is shown in FIG. 2 and SEQ ID NO: 2 in the sequence listing. For convenience of explanation, the wild-type glycine oxidase is abbreviated as "WT-GOX".

Comparative Example 2

The specific activity, thermal stability, and kinetic constant $K_m$ of a commercially available glycine oxidase, product number H244K manufactured by BioVision, Inc, were evaluated as described above. The results are shown in Table 1, the specific activity is shown in FIG. 3A, and thermal stability is shown in FIG. 3B.

Here, H244K is a mutant enzyme in which a mutation is introduced into a wild-type glycine oxidase derived from *B. subtilis*, a *Bacillus* bacterium that is not a thermophilic bacterium, and the introduction of mutation is performed by the method described in Non-PTL 2.

TABLE 1

| Enzyme | | Specific activity | Thermal stability | Kinetic constant $K_m$ |
|---|---|---|---|---|
| Comparative Example 1 | WT-GOX | 0.7 U/mg | Up to 60° C. | 0.25 mM |
| Comparative Example 2 | H244K | 1.2 U/mg | Up to 45° C. | 0.14 mM |
| Example 1 | V-GOX1 | 4.0 U/mg | Up to 70° C. | 0.20 mM |

Example 1

As described in the above embodiment, in WT-GOX of Comparative Example 1, it was revealed that a 248th (position 248) to 255th (position 255) partial amino acid sequence in the amino acid sequence represented by SEQ ID NO: 1 is a characteristic region unique to thermophilic bacteria belonging to the family *Bacillus*. Therefore, a mutation was introduced into the characteristic region of WT-GOX based on the method described in Non-PTL 2, and a plasmid vector containing a glycine oxidase gene into which a mutation was randomly introduced was obtained. For convenience of explanation, the mutant glycine oxidase is abbreviated as "V-GOX" in this example.

Thus, the plasmid vector was introduced into the above host cell (*E. coli* BL21 (DE3)) based on the method described in Non-PTL 1, and expression of V-GOX was confirmed. When the enzyme activity was confirmed for 204 types among the obtained colonies, 14 types of colonies expressing V-GOXs showing high activity were confirmed. Therefore, these 14 types of V-GOXs were sequentially analyzed, and their enzyme activities were measured.

As a result, as shown in Table 2, 8 types of V-GOXs (V-GOX1 to V-GOX8) could be identified. In these V-GOXs, the 251st (position 251) amino acid in the amino acid sequence represented by SEQ ID NO: 1 is substituted from glycine (Gly, G) to another amino acid. The enzyme activity in Table 2 is shown as the ratio (times) of the enzyme reaction rate (use of crude enzyme solution) of V-GOX when WT-GOX is used as reference (1).

TABLE 2

| Enzyme | Codon | Amino acid | Enzyme activity (times) |
|---|---|---|---|
| V-GOX1 | CAA | Glutamine (Gln, Q) | 8.2 |
| V-GOX2 | ATA | Isoleucine (Ile, I) | 7.3 |
| V-GOX3 | CGT | Arginine (Arg, R) | 5.1 |
| V-GOX4 | CAC | Histidine (His, H) | 4.8 |
| V-GOX5 | ACA | Threonine (Thr, T) | 4.5 |
| V-GOX6 | GCC | Alanine (Ala, A) | 3.4 |
| V-GOX7 | AAC | Asparagine (Asn, N) | 3.3 |
| V-GOX8 | GAG | Glutamic acid (Glu, E) | 2.6 |
| WT-GOX | GGC | Glycine (Gly, G) | 1 |

Among these V-GOX1 to V-GOX8, V-GOX1 having an amino acid sequence in which the 251st (position 251) amino acid was substituted from glycine (Gly, G) to glutamine (Gln, Q) showed the highest enzyme activity. Therefore, after purifying this V-GOX1, the molecular weight (SDS-PAGE), the optimum temperature, the optimum pH, thermal stability, pH stability, the specific activity, and the kinetic constant $K_m$ were evaluated. The results of the specific activity, thermal stability, and the kinetic constant $K_m$ are shown in Table 1 above, the specific activity is shown in FIG. 3A, and thermal stability is shown in FIG. 3B, and further, evaluation results of enzyme properties of V-GOX1 containing them are also shown in Table 3 together with the conditions.

TABLE 3

| Enzyme properties | Conditions | Numerical value |
|---|---|---|
| Molecular weight | SDS-PAGE | 40 kDa |
| Optimum temperature | PPi, pH 8.5, reacted for 15 minutes | 45° C. |
| Optimum pH | PPi, 40° C., reacted for 15 minutes | pH 8.0 |
| Thermal stability | PPi, pH 8.5, retained for 1 hour | Up to 70° C. |
| pH Stability | PPi, 4° C., reacted for 24 hours | pH 5.5-10.0 |
| Specific activity | — | 4.0 U/mg |
| Kinetic constant $K_m$ | — | 0.2 mM |

* PPi: Pyrophosphate (Comparison Between Examples and Comparative Examples)

As is clear from Table 1 and FIGS. 3A and 3B, the enzyme of Comparative Example 1, that is, WT-GOX derived from HTA426 has thermal stability 15° C. higher as compared with the enzyme of Comparative Example 2, that is, H244K, a commercially available mutant glycine oxidase derived from *Bacillus subtilis* that is not a thermophilic bacterium, and although WT-GOX exhibits excellent thermal stability, its specific activity is greatly inferior. Further, regarding the kinetic constant $K_m$, the WT-GOX of Comparative Example 1 is higher than H244K of Comparative Example 2.

In contrast, V-GOX1, which had the highest activity among the enzymes of Example 1, had a specific activity 5.7 times that of the WT-GOX of Comparative Example 1 and 3.3 times that of the H244K of Comparative Example 2. Further, thermal stability of V-GOX1 is 10° C. higher than that of the WT-GOX of Comparative Example 1, and 25° C. higher than that of the H244K of Comparative Example 2. Moreover, the kinetic constant $K_m$ of V-GOX1 is a value lower than that of the WT-GOX of Comparative Example 1, and it can be said that it is a value comparable to the value of the H244K of Comparative Example 2.

In addition, as is clear from Table 2, among WT-GOX amino acid sequences, the mutant enzymes V-GOX1 to V-GOX8 obtained by introducing a mutation into the characteristic region of thermophilic bacteria belonging to the family *Bacillus* all have higher enzyme activity than WT-GOX. Even V-GOX8, which has the lowest enzyme activity among these eight types, has a reaction rate 2.5 times or more that of WT-GOX.

Also, V-GOXs2 to 8 have substantially the same enzyme properties as V-GOX1 shown in Table 3, although not specifically shown. Therefore, not only V-GOX1, but also seven types of enzymes, V-GOXs2 to 8, have both excellent enzyme activity and excellent thermal stability, and also have a value of kinetic constant $K_m$ that does not greatly differ from those of conventional mutant enzymes. Therefore, it can be seen that V-GOXs1 to 8 are characteristic mutant enzymes having enzyme properties as shown in Table 3 as compared with WT-GOX.

Furthermore, as is clear from Table 2, in V-GOXs1 to 8, glycine (G), the 251st (position 251) amino acid of WT-GOX is substituted with any of various amino acids, that is alanine (A), glutamic acid (E), histidine (H), isoleucine (I), asparagine (N), glutamine (Q), arginine (R), or threonine (T). Therefore, it can be seen that V-GOX having higher activity than WT-GOX is obtained by substituting glycine with an amino acid other than glycine. In particular, it can be also seen that highly active V-GOX can be easily obtained by substituting glycine with any of the above eight types.

In addition, amino acids substituted from glycine in V-GOXs1 to 5 having relatively high enzyme activity are basic or hydrophobic amino acids. That is, glutamine, which is a substituted amino acid of V-GOX1, arginine, which is a substituted amino acid of V-GOX3, and histidine, which is a substituted amino acid of V-GOX4, are all basic amino acids, and isoleucine, which is a substituted amino acid of V-GOX2, and threonine, which is a substituted amino acid of V-GOX5, are both hydrophobic amino acids. Therefore, it can be seen that the amino acid substituted from glycine in WT-GOX is preferably a basic amino acid or a hydrophobic amino acid.

It should be noted that the present invention is not limited to the description of the above-described embodiment, and various modifications are possible within the scope shown in the scope of the claims, and are disclosed in different embodiments and a plurality of modifications. Embodiments obtained by appropriately combining the technical means are also included in the technical scope of the present invention.

In addition, from the above description, many modifications and other embodiments of the present invention are obvious to those skilled in the art. Accordingly, the foregoing description should be construed as illustrative only and is provided for the purpose of teaching those skilled in the art the best mode of carrying out the invention. The details of the structure and/or function can be modified substantially without departing from the spirit of the invention.

INDUSTRIAL APPLICABILITY

The present invention can be widely used suitably in the field related to the mutant glycine oxidase that achieves both good enzyme activity and good thermal stability, obtained by introducing a mutation into a glycine oxidase derived from thermophilic bacteria of the family *Bacillus*, including thermophilic bacteria of the genus *Bacillus* or the genus *Geobacillus*.

---

The invention claimed is:

1. A mutant glycine oxidase
which is a mutant enzyme in which a glycine at the 251st position of an amino acid sequence having at least 95% sequence identity to SEQ ID NO: 1, in an amino acid motif of asparagine (N), glycine (G), cysteine (C), and tyrosine (Y), of a wild-type glycine oxidase derived from thermophilic bacteria selected from a group consisting of *Geobacillus kaustophilus*, *Geobacillus stearothermophilus*, and *Geobacillus thermoleovorans* is substituted with another amino acid, the mutant glycine oxidase having:
a molecular weight of 40,000±2,000 daltons in sodium dodecyl sulphate-polyacrylamide gel electrophoresis (SDS-PAGE);
an optimum temperature of 45° C. under a condition of pH 8.5 in presence of pyrophosphate;
an optimum pH of pH 8.0 under a condition of 37° C. in presence of pyrophosphate;
a thermal stability being stable up to 70° C. under a condition of pH 8.5 while retaining for 1 hour in presence of pyrophosphate;
a pH stability being stable in a range of pH 5.5 to 10.0 under a condition of 4° C. while retaining for 24 hours in presence of pyrophosphate;
a specific activity of at least 1.2 units/mg; and
a kinetic constant (Michaelis constant) $K_m$ of 0.2 mM or less.

2. A mutant glycine oxidase
which is a mutant enzyme of glycine oxidase derived from thermophilic bacteria belonging to the family *Bacillus*, the mutant glycine oxidase having at least 95% sequence identity to SEQ ID NO: 1, and the mutant glycine oxidase having an amino acid sequence in which a 251st amino acid in SEQ ID NO: 1 is substituted from glycine to another amino acid.

3. The mutant glycine oxidase according to claim 2, in which the 251st amino acid is substituted from glycine to a basic amino acid or a hydrophobic amino acid.

4. The mutant glycine oxidase according to claim 3, wherein
the basic amino acid is glutamine, arginine, or histidine, and the hydrophobic amino acid is isoleucine or threonine.

5. The mutant glycine oxidase according to claim 2, wherein
the another amino acid is alanine, glutamic acid, histidine, isoleucine, asparagine, glutamine, arginine, or threonine.

6. A DNA sequence encoding the mutant glycine oxidase according to claim 1.

7. A replicable recombinant vector comprising the DNA sequence according to claim 6 and an autonomously replicating sequence.

8. A cell expressing the mutant glycine oxidase obtained by introducing the DNA sequence according to claim 6 into a host cell.

9. A method for producing a mutant glycine oxidase, comprising
culturing the host cell according to claim 8, and collecting the mutant glycine oxidase from the resulting culture.

10. A cell obtained by introducing the recombinant DNA vector according to claim 7 into a host cell.

11. The mutant glycine oxidase according to claim 2, wherein
The thermophilic bacteria belonging to the family *Bacillus* is a bacteria belonging to one of genus *Bacillus*, genus *Alicyclobacillus*, genus *Brevibacillus*, genus *Geobacillus*, genus *Sulfobacillus*, genus *Paenibacillus*, and genus *Salinicoccus*.

12. A DNA sequence encoding the mutant glycine oxidase according to claim 2.

13. A replicable recombinant vector comprising the DNA sequence according to claim 12 and an autonomously replicating sequence.

14. A cell obtained by introducing the DNA sequence according to claim 12.

15. A method for producing a mutant glycine oxidase, comprising
culturing the cell according to claim 14, and collecting the mutant glycine oxidase from the resulting culture.

16. A cell obtained by introducing the recombinant DNA vector according to claim 13 into a host cell.

* * * * *

SEQUENCE LISTING

<160> NUMBER OF SEQ ID NOS: 4

<210> SEQ ID NO 1
<211> LENGTH: 377
<212> TYPE: PRT
<213> ORGANISM: Geobacillus kaustophilius HTA426

<400> SEQUENCE: 1

```
Met Thr His Arg Tyr Asp Val Ala Ile Val Gly Gly Gly Val Ile Gly
1               5                   10                  15

Ala Ala Ile Gly Phe Glu Leu Ala Lys Arg Arg His Arg Val Ala Ile
            20                  25                  30

Phe Glu Lys Gly Thr Met Gly Ser Gly Ala Ser Ser Ala Ala Ala Gly
        35                  40                  45

Met Leu Gly Ala Gln Ser Glu Phe Ser Thr Ser Ser Pro Leu Val Pro
    50                  55                  60

Leu Ala Leu Gln Ser Arg Ala Leu Met Pro Ala Leu Ala Glu Glu Leu
65                  70                  75                  80

Arg Glu Arg Thr Gly Ile Asp Ile Gly Leu Val Glu Lys Gly Leu Ile
                85                  90                  95

Lys Leu Ala Thr Thr Glu Glu Ala Asp Asp Leu Tyr Arg His Tyr
            100                 105                 110

Thr Phe Trp Arg Gly Ile Gly Glu Pro Val Gln Trp Leu Thr Lys Gly
        115                 120                 125

Glu Ala Leu Glu Met Glu Pro Arg Leu Ala Ala Glu Ala Leu Ala Gly
    130                 135                 140

Ala Met Tyr Ile Pro Gly Asp Gly Gln Val Ser Ala Pro Asp Leu Ala
145                 150                 155                 160

Ala Ala Leu Ala Tyr Ala Ala Ala Ser Ala Gly Ala Cys Leu Tyr Glu
                165                 170                 175

Tyr Thr Glu Val Phe Asp Ile Arg Ser Asp Ser Ser Gly His Val Leu
            180                 185                 190

Asp Thr Thr Gly Gly Thr Phe Ala Ala Glu Ala Val Val Ile Ala Ser
        195                 200                 205

Gly Ala Trp Ala Ala Arg Leu Gly Ala Arg Val Gly Leu Ser Leu Ser
    210                 215                 220

Val Tyr Pro Val Lys Gly Glu Cys Val Met Val Arg Ala Pro Val Pro
225                 230                 235                 240

Leu Leu Gln Thr Thr Val Phe Ala Lys Asn Gly Cys Tyr Ile Val Pro
                245                 250                 255

Lys Ser Gly Asn Arg Leu Leu Ile Gly Ala Thr Ser Thr Pro Gly Thr
            260                 265                 270
```

```
Phe Asp Arg Arg Val Ser Ala Gly Gly Val Met Asn Leu Leu His Arg
        275                 280                 285

Ala Ala His Leu Val Pro Asp Ile Glu Gln Ala Glu Trp Val Ala Ser
    290                 295                 300

Trp Ser Gly Ile Arg Pro Gln Thr Glu Asp Gly Leu Pro Tyr Leu Gly
305                 310                 315                 320

Glu His Pro Glu Arg Arg Gly Leu Phe Val Ala Ala Gly His Tyr Arg
                325                 330                 335

Asn Gly Ile Leu Leu Ser Pro Leu Thr Gly Leu Leu Val Ala Asp Leu
            340                 345                 350

Val Glu Arg Lys Glu Thr Ala Phe Asp Leu Ala Pro Phe Ser Leu Thr
        355                 360                 365

Arg His Ile Gly Lys Val Gly Val Glu
        370                 375
```

```
<210> SEQ ID NO 2
<211> LENGTH: 1134
<212> TYPE: DNA
<213> ORGANISM: Geobacillus kaustophilus HTA426

<400> SEQUENCE: 2
atgacgcatc ggtatgacgt cgccatcgtc ggcggcgggg tgattggggc ggccatcggt     60
tttgagctcg ccaagcggcg gcatcgcgtc gccatttttg aaaaaggaac gatgggaagc    120
ggggcgtcaa gcgcggcagc cggcatgctt ggggcgcaat ccgagttttc gacgtcaagc    180
ccgcttgtgc cgcttgcctt gcaaagccga gctctcatgc cggccttggc tgaagagctg    240
agggagagga ccggcatcga tatcggcctt gtcgaaaaag gattgatcaa actagcgaca    300
acggaagagg aagcagacga tctctatcgc cattatacat tttggcgggg cataggcgaa    360
ccggtgcagt ggctcacgaa aggggaggcg cttgaaatgg agccgcgtct tgcggcggaa    420
gcgcttgccg gcgcgatgta catccctggc gatgggcaag tgagcgctcc ggatttggcc    480
gccgctcttg cctatgccgc cgcctccgcc ggcgcttgtc tgtacgagta tcggaagtg    540
ttcgacatcc gttccgacag cagtgggcat gtgttagaca caacaggcgg gacgtttgcc    600
gccgaggcgg tcgtcatcgc ttccggcgct tgggcggcgc ggctcggcgc gcgggtcggg    660
ctttcgcttt ccgtttatcc ggtcaaagga gaatgcgtca tggtgcgcgc cccggttccg    720
ttgttgcaaa cgactgtatt tgcgaaaaac ggctgctaca tcgttccgaa atcaggaaac    780
cggctgctca tcggagcgac gtccacgccc ggcacgttcg atcgacgtgt atcggccggt    840
ggggtgatga acttgcttca ccgcgccgcc caccttgttc cggacatcga acaggcggaa    900
tgggtggcat catggagcgg cattcggccg cagaccgaag acggcttgcc ttatctaggc    960
gagcatccgg agcggcgcgg cttattcgtc gctgccggcc attaccggaa cggcattttg   1020
ctcagcccat tgaccggtct gcttgtcgcc gacttagtgg agcggaaaga gacggcgttt   1080
gatcttgcgc catttcgtt gacacgccat atcggaaagg tggggtgga atga           1134
```

```
<210> SEQ ID NO 3
<211> LENGTH: 377
<212> TYPE: PRT
<213> ORGANISM: Artificial Sequence
<220> FEATURE:
<223> OTHER INFORMATION: The source of protein sequence is Geobacillus
      kaustophilius HTA426.
<220> FEATURE:
<221> NAME/KEY: VARIANT
<222> LOCATION: (251)..(251)
```

<223> OTHER INFORMATION: Xaa is a basic or hydrophobic amino acid, not glycine.

<400> SEQUENCE: 3

```
Met Thr His Arg Tyr Asp Val Ala Ile Val Gly Gly Val Ile Gly
1               5                   10                  15

Ala Ala Ile Gly Phe Glu Leu Ala Lys Arg Arg His Arg Val Ala Ile
            20                  25                  30

Phe Glu Lys Gly Thr Met Gly Ser Gly Ala Ser Ser Ala Ala Gly
            35                  40                  45

Met Leu Gly Ala Gln Ser Glu Phe Ser Thr Ser Ser Pro Leu Val Pro
    50                  55                  60

Leu Ala Leu Gln Ser Arg Ala Leu Met Pro Ala Leu Ala Glu Glu Leu
65                  70                  75                  80

Arg Glu Arg Thr Gly Ile Asp Ile Gly Leu Val Glu Lys Gly Leu Ile
                85                  90                  95

Lys Leu Ala Thr Thr Glu Glu Glu Ala Asp Asp Leu Tyr Arg His Tyr
                100                 105                 110

Thr Phe Trp Arg Gly Ile Gly Glu Pro Val Gln Trp Leu Thr Lys Gly
            115                 120                 125

Glu Ala Leu Glu Met Glu Pro Arg Leu Ala Ala Glu Ala Leu Ala Gly
    130                 135                 140

Ala Met Tyr Ile Pro Gly Asp Gly Gln Val Ser Ala Pro Asp Leu Ala
145                 150                 155                 160

Ala Ala Leu Ala Tyr Ala Ala Ala Ser Ala Gly Ala Cys Leu Tyr Glu
                165                 170                 175

Tyr Thr Glu Val Phe Asp Ile Arg Ser Asp Ser Ser Gly His Val Leu
            180                 185                 190

Asp Thr Thr Gly Gly Thr Phe Ala Ala Glu Ala Val Val Ile Ala Ser
    195                 200                 205

Gly Ala Trp Ala Ala Arg Leu Gly Ala Arg Val Gly Leu Ser Leu Ser
210                 215                 220

Val Tyr Pro Val Lys Gly Glu Cys Val Met Val Arg Ala Pro Val Pro
225                 230                 235                 240

Leu Leu Gln Thr Thr Val Phe Ala Lys Asn Xaa Cys Tyr Ile Val Pro
                245                 250                 255

Lys Ser Gly Asn Arg Leu Leu Ile Gly Ala Thr Ser Thr Pro Gly Thr
            260                 265                 270

Phe Asp Arg Arg Val Ser Ala Gly Val Met Asn Leu Leu His Arg
            275                 280                 285

Ala Ala His Leu Val Pro Asp Ile Glu Gln Ala Glu Trp Val Ala Ser
    290                 295                 300

Trp Ser Gly Ile Arg Pro Gln Thr Glu Asp Gly Leu Pro Tyr Leu Gly
305                 310                 315                 320

Glu His Pro Glu Arg Arg Gly Leu Phe Val Ala Ala Gly His Tyr Arg
                325                 330                 335

Asn Gly Ile Leu Leu Ser Pro Leu Thr Gly Leu Leu Val Ala Asp Leu
            340                 345                 350

Val Glu Arg Lys Glu Thr Ala Phe Asp Leu Ala Pro Phe Ser Leu Thr
                355                 360                 365

Arg His Ile Gly Lys Val Gly Val Glu
    370                 375
```

<210> SEQ ID NO 4

```
<211> LENGTH: 1134
<212> TYPE: DNA
<213> ORGANISM: Artificial Sequence
<220> FEATURE:
<223> OTHER INFORMATION: The source of genetic material is Geobacillus
      kaustophilius HTA426.
<220> FEATURE:
<221> NAME/KEY: CDS
<222> LOCATION: (751)..(753)
<223> OTHER INFORMATION: Each n can be a or t or c or g. The nucleotides
      at positions 751-753 correspond to the codon of the amino acid
      encoded by Xaa at position 251 of SEQ ID NO 3.

<400> SEQUENCE: 4
atgacgcatc ggtatgacgt cgccatcgtc ggcggcgggg tgattggggc ggccatcggt       60
tttgagctcg ccaagcggcg gcatcgcgtc gccattttg aaaaaggaac gatgggaagc      120
ggggcgtcaa gcgcggcagc cggcatgctt ggggcgcaat ccgagttttc gacgtcaagc      180
ccgcttgtgc cgcttgcctt gcaaagccga gctctcatgc cggccttggc tgaagagctg      240
agggagagga ccggcatcga tatcggcctt gtcgaaaaag gattgatcaa actagccgaca     300 acggaagagg aagcagacga tctctatcgc cattatacat tttggcgggg cataggcgaa      360
ccggtgcagt ggctcacgaa aggggaggcg cttgaaatgg agccgcgtct tgcggcggaa      420
gcgcttgccg gcgcgatgta catccctggc gatgggcaag tgagcgctcc ggatttggcc      480
gccgctcttg cctatgccgc cgcctccgcc ggcgcttgtc tgtacgagta tacggaagtg      540
ttcgacatcc gttccgacag cagtgggcat gtgttagaca caacaggcgg gacgtttgcc      600
gccgaggcgg tcgtcatcgc ttccggcgct tgggcggcgc ggctcggcgc gcgggtcggg      660
ctttcgcttt ccgtttatcc ggtcaaagga gaatgcgtca tggtgcgcgc cccggttccg      720
ttgttgcaaa cgactgtatt tgcgaaaaac nnntgctaca tcgttccgaa atcaggaaac      780
cggctgctca tcggagcgac gtccacgccc ggcacgttcg atcgacgtgt atcggccggt      840
ggggtgatga acttgcttca ccgcgccgcc caccttgttc cggacatcga acaggcggaa      900
tgggtggcat catggagcgg cattcggccg cagaccgaag acggcttgcc ttatctaggc      960
gagcatccgg agcggcgcgg cttattcgtc gctgccggcc attaccggaa cggcatttg      1020 ctcagcccat tgaccggtct gcttgtcgcc gacttagtgg agcggaaaga gacggcgttt     1080
gatcttgcgc cattttcgtt gacacgccat atcggaaagg tgggggtgga atga            1134
```